(12) United States Patent
Rajadhyaksha et al.

(10) Patent No.: US 8,853,456 B2
(45) Date of Patent: Oct. 7, 2014

(54) PROCESS FOR THE PREPARATION OF TAPENTADOL

(75) Inventors: Mangesh Narayan Rajadhyaksha, Mumbai (IN); Ranjeet Nair, Mumbai (IN); Sandip Kacharu Deshmukh, Mumbai (IN); Somnath Ambadas Khabale, Mumbai (IN); Aditi Milind Panandikar, Mumbai (IN)

(73) Assignee: Indoco Remedies Limited, Mumbai, IN (US)

( * ) Notice: Subject to any disclaimer, the term of this patent is extended or adjusted under 35 U.S.C. 154(b) by 0 days.

(21) Appl. No.: 13/816,292

(22) PCT Filed: Aug. 16, 2011

(86) PCT No.: PCT/IN2011/000546
§ 371 (c)(1),
(2), (4) Date: Feb. 11, 2013

(87) PCT Pub. No.: WO2012/023147
PCT Pub. Date: Feb. 23, 2012

(65) Prior Publication Data
US 2013/0137890 A1    May 30, 2013

(30) Foreign Application Priority Data
Aug. 16, 2010 (IN) .......................... 2303/MUM/2010

(51) Int. Cl.
*C07C 211/27* (2006.01)
*C07C 213/00* (2006.01)
*C07C 309/66* (2006.01)
*C07C 309/73* (2006.01)

(52) U.S. Cl.
CPC ............. *C07C 213/00* (2013.01); *C07C 309/66* (2013.01); *C07C 309/73* (2013.01)
USPC ......................................... 564/374; 564/336

(58) Field of Classification Search
USPC .................................................. 564/336, 374
See application file for complete search history.

(56) References Cited

U.S. PATENT DOCUMENTS 8,263,809 B2 * 9/2012 Hell .............................. 564/443

FOREIGN PATENT DOCUMENTS

| CN | 101948397 A | 1/2011 |
|---|---|---|
| EP | 0693475 A | 1/1996 |
| WO | 2004108658 A | 12/2004 |
| WO | 2005000788 A | 1/2005 |
| WO | 2008012046 A | 1/2008 |
| WO | 2008012047 A | 1/2008 |

OTHER PUBLICATIONS

Ghislandi, Chirality, vol. 6, 1994, p. 389-399.*
Sajiki, Organic Letters, 2006, vol. 8, No. 5, p. 987-990.*
International Search Report dated Oct. 28, 2011 issued for PCT/IN2011/000546.

* cited by examiner

*Primary Examiner* — Rebecca Anderson
*Assistant Examiner* — Karen Cheng
(74) *Attorney, Agent, or Firm* — Kramer Amado, P.C.

(57) ABSTRACT

Disclosed herein is an improved process for the preparation of 3-[(2R,3R)-1-(dimethylamino)-2-methylpentan-3-yl]phenol of Formula-I and its pharmaceutically acceptable salt which comprises the reaction of (S)-1-(dimethylamino)-2-methylpentan-3-one of formula VIII with 3-bromo anisole of formula II under Grignard conditions to get the compound (2S,3R)-1-(dimethylamino)-3-(3-methoxyphenyl)-2-methyl pentan-3-ol of formula V followed by activation of the —OH group of the formula V to convert into sulfonate esters of formula IX, which are on reductive deoxygenation to yield (2R,3R)-3-(3-methoxyphenyl)-N,N,2-trimethylpentan-1-amine of formula VII and demethylation of formula VII to obtain the compound 3-[(2R,3R)-1-(dimethylamino)-2-methylpentan-3-yl]phenol of Formula-1.

15 Claims, No Drawings

PROCESS FOR THE PREPARATION OF TAPENTADOL

FIELD OF INVENTION

The present invention relates to the improved process for the preparation of 3-[(2R,3R)-1-(dimethylamino)-2-methylpentan-3-yl]phenol of Formula-I and its pharmaceutically acceptable salt.

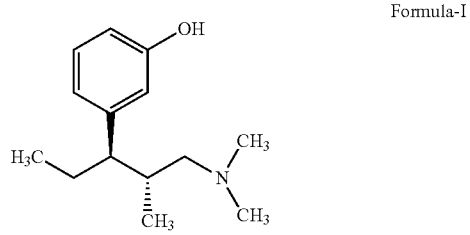 [SMILES: CC[C@@H](c1cccc(O)c1)[C@@H](C)CN(C)C]

Formula-I

BACKGROUND AND PRIOR ART

The compound 3-[(2R,3R)-1-(dimethylamino)-2-methylpentan-3-yl]phenol of Formula-I and its hydrochloride salt having international non proprietary name as tapentadol hydrochloride is a centrally-acting analgesic with a dual mode of action as an agonist at the μ-opioid receptor and as a norepinephrine reuptake inhibitor.

The compound was first time disclosed in patent EP0693475; wherein 3-bromo anisole of Formula-II is reacted with 1,1-dimethylamino-2-methylpentan-3-one of Formula-III under conditions of Grignard reaction to obtain racemic 1-(dimethylamino)-3-(3-methoxyphenyl)-2-methylpentan-3-ol hydrochloride of Formula-IV. The compound of Formula-IV is converted to its base and subjected to enantiomeric separation using chiral HPLC column to obtain (2S, 3R)-1-(dimethylamino)-3-(3-methoxyphenyl)-2-methylpentan-3-ol of Formula-V, which on chlorination using thionyl chloride forms (2S,3R)-3-chloro-3-(3-methoxyphenyl)-N,N,2-trimethylpentan-1-amine of Formula-VI. The compound of Formula-VI on reaction with zinc borohydride or tin cyanoborohydride results in the formation of (2R,3R)-3-(3-methoxyphenyl)-N,N,2-trimethylpentan-1-amine of Formula-VII. The compound of Formula-VII on heating with concentrated hydrobromic acid results in the compound 3-[(2R,3R)-1-(dimethylamino)-2-methylpentan-3-yl]phenol of Formula-I. Throughout the reaction the intermediate salt formation wherever required and final hydrochloride salt preparation is done using trimethylchloro silane The reaction sequence is as represented in scheme-1 below.

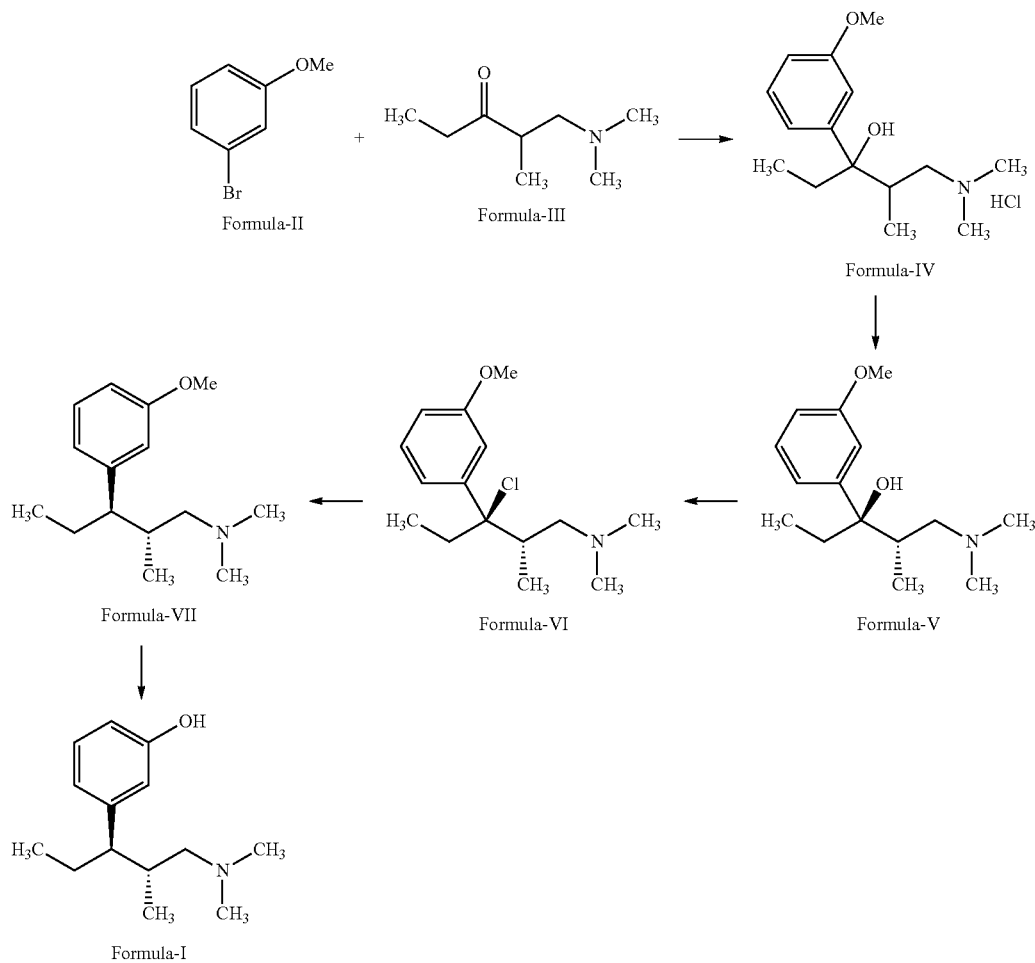

The drawback of the above invention is the use of chiral HPLC column to separate the required enantiomer and use of trimethylchloro silane for preparation of hydrochloride salt which renders the process industrially uneconomical.

WO2004/108658 ('658) describes process for the preparation of (2R,3R)-3-(3-methoxyphenyl)-N,N,2-trimethylpentan-1-amine of Formula-VII, the penultimate intermediate to prepare tapentadol, wherein the compound (2S,3S)-1-dimethylamino-3-(3-methoxyphenyl)-2-methylpentan-3-ol of Formula-VA, is heated in acidic medium to get intermediate compound (Z,E)-(S)-[3-(3-methoxyphenyl)-2-methyl-pent-3-enyl]-dimethylamine HCl of Formula-X, which on catalytic hydrogenation yields enantiomeric mixture of (2R,3R)-3-(3-methoxyphenyl)-N,N,2-trimethylpentan-1-amine of Formula-VII and (2R,3S))-3-(3-methoxyphenyl)-N,N,2-trimethylpentan-1-amine of Formula-VIIA. The required stereoisomer is separated to get (2R,3R)-3-(3-methoxyphenyl)-N,N,2-trimethylpentan-1-amine of Formula-VII, which can be treated with concentrated hydrobromic acid to get tapentadol. The reaction sequence is as per scheme-2 below;

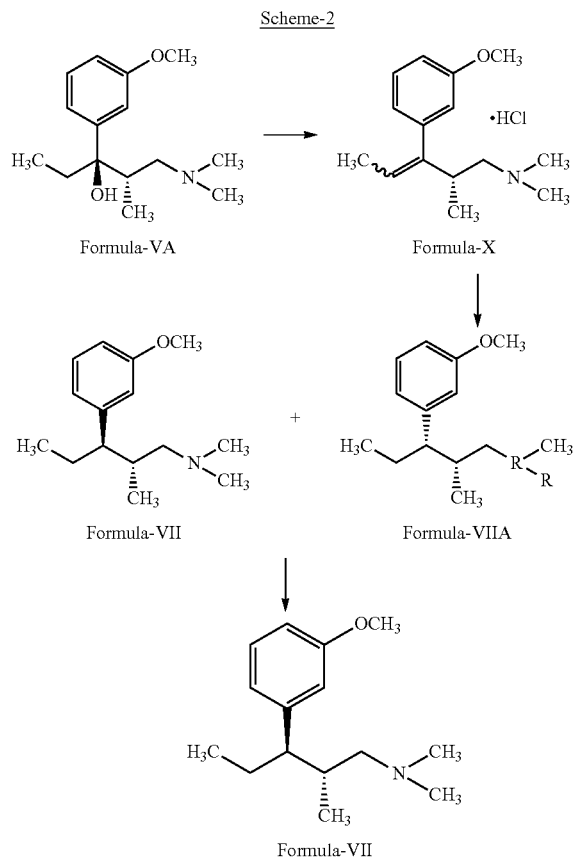

WO2005/000788 ('788) describes another method of preparing tapentadol, wherein compound (2S,3S)-1-(dimethylamino)-3-(3-methoxyphenyl)-2-methyl-3-pentanol of Formula-VA is subjected to dehydration reaction using heterogeneous catalyst to get intermediate compound (Z,E)-(S)-[3-(3-methoxyphenyl)-2-methyl-pent-3-enyl]-dimethyl amine hydrochloride of Formula-X, which on catalytic reduction yields enantiomeric mixture of (2R,3R)-3-(3-methoxyphenyl)-N,N,2-trimethylpentan-1-amine of Formula-VII and (2R,3S))-3-(3-methoxyphenyl)-N,N,2-trimethylpentan-1-amine of Formula-VIIA The required stereoisomer is separated to get (2R,3R)-3-(3-methoxyphenyl)-N,N,2-trimethylpentan-1-amine Formula-VII.

The drawback of the above invention as disclosed in '658 and '788 is the formation of mixtures of distereoisomer (2R, 3R)-3-(3-methoxyphenyl)-N,N,2 trimethylpentan-1-amine and (2R,3S)-3-(3-methoxyphenyl)-N,N,2 trimethylpentan-1-amine during the preparation which requires separation of the required stereoisomer resulting in lower yield and the unwanted isomer is left as it is thus affecting the economy of the process.

WO2008/012046 describes another method for the preparation of tapentadol, wherein 1-(3-(benzyloxy)phenyl)propan-1-one is reacted with N-Methyl-N-methylene-methaneaminium chloride in presence of acetyl chloride and solvent acetonitrile to obtain compound 1-(3-(benzyloxy)phenyl)-3-(dimethylamino)-2-methylpropan-1-one. The compound is resolved with L-(−)-dibenzoyltartaric acid to get (S)-1-(3-(benzyloxy)phenyl)-3-(dimethylamino)-2-methylpropan-1-one. The isolated compound is then reacted with ethyl magnesium bromide undergoing Grignard reaction to isolate (2S,3R)-3-(3-(benzyloxy)phenyl)-1-(dimethylamino)-2-methylpentan-3-ol, which on reaction with trifluoroacetic anhydride in acetic acid results in acetylated compound. The acetylated compound on hydrogenolysis results in the compound 3-[(2R,3R)-1-(dimethylamino)-2-methylpentan-3-yl]phenol of Formula-I.

The drawback of the above invention involves in use of costly reagent and solvents trifluoroacetic anhydride for acetylation of alcoholic —OH group and acetonitrile solvent for the condensation reaction affecting economy of the process on industrial scale.

WO2008012047 describes yet another method for the preparation of tapentadol, wherein 1-(3-methoxyphenyl)propan-1-one is reacted with dimethyl amine hydrochloride and paraformaldehyde under Mannich reaction condition to get 3-(dimethylamino)-1-(3-methoxyphenyl)-2-methylpropan-1-one hydrochloride, which after reacting with sodium hydroxide is reacted with (2R,3R)—O,O'-dibenzoyl tartaric acid monohydrate to get (S)-3-(dimethylamino)-1-(3-methoxyphenyl)-2-methylpropan-1-one L-(−)-dibenzoyltartarate. The dibenzoyl tartrate salt is further reacted with diethyl amine to isolate keto compound (S)-3-(dimethylamino)-1-(3-methoxyphenyl)-2-methylpropan-1-one. The keto compound is reacted with ethyl magnesium halide under Grignard condition to isolate the compound (2S,3R)-1-(dimethylamino)-3-(3-methoxyphenyl)-2-methylpentan-3-ol. The hydrochloride salt of the compound (2S,3R)-1-(dimethylamino)-3-(3-methoxyphenyl)-2-methylpentan-3-ol on reaction with aqueous hydrochloric acid undergoes dehydration yielding the compound (R)-3-(3-methoxyphenyl)-N,N,2-trimethylpent-3-en-1-amine, which after hydrogenation using homogeneous or heterogeneous catalyst results in the mixture of compound (2R,3R))-3-(3-methoxyphenyl)-N,N,2-trimethylpentan-1-amine and (2R,3S)-3-(3-methoxyphenyl)-N,N,2-trimethylpentan-1-amine having Z:E ratio of 5.5:1. The required compound (2R,3R)-3-(3-methoxyphenyl)-N,N,2-trimethylpentan-1-amine is separated from the mixture by making hydrochloride salt. The isolated salt is dissolved in methane sulphonic acid and treated with methionine to get the compound 3-[(2R,3R)-1-(dimethylamino)-2-methylpentan-3-yl]phenol of Formula-I, which is isolated as hydrochloride salt of tapentadol hydrochloride.

The drawbacks of the above process are,
i. resolution of the racemic intermediate using chiral reagent increases the reaction steps;

ii. mixtures of distereoisomer require resolution and separation of the required stereoisomer resulting in lower yield and the unwanted isomer is left as it is affecting the economy of the process.

Therefore, there remains a need for an improved process for preparing the compound 3-[(2R,3R)-1-(dimethylamino)-2-methylpentan-3-yl]phenol of Formula-I that eliminates or substantially reduces the number of steps, overcomes resolution and separation of stereoisomer, avoids chromatographic separation of required enantiomer and employs safe and economical reagents for the reaction.

Thus, the present inventors have come out with an improved process which ameliorates the problems in the prior art by using a stereospecific reaction conditions to avoid the resolution, and carrying out chemical purification thus avoiding the chromatographic separation of the required enantiomer and use of catalyst for reductive deoxygenation to improve safety and cleaner reaction.

OBJECTIVE OF THE INVENTION

The main objective of the present invention is to prepare 3-[(2R,3R)-1-(dimethylamino)-2-methylpentan-3-yl]phenol of Formula-I and its pharmaceutically acceptable salt by robust, rigid and industrial friendly process.

Another objective of the present invention is to prepare stereospecific and optically pure intermediate compound (2S,3R)-1-(dimethylamino)-3-(3-methoxyphenyl)-2-methylpentan-3-ol of Formula-V;

Yet another objective of the present invention is to prepare novel intermediate compound (2S,3R)-1-(dimethylamino)-3-(3-methoxyphenyl)-2-methylpentan-3-yl methane sulfonate of Formula IXA.

Yet another objective of the present invention is to prepare novel intermediate compound (2S,3R)-1-(dimethylamino)-3-(3-methoxyphenyl)-2-methyl-pentan-3-yl 4-methylbenzene sulfonate of Formula IXB.

SUMMARY OF THE INVENTION

Accordingly the present invention provides a process for the preparation of 3-[(2R,3R)-1-(dimethylamino)-2-methylpentan-3-yl]phenol of Formula-I

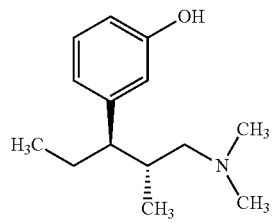

Formula-I comprising a step of;
i. reacting (S)-1-(dimethylamino)-2-methylpentan-3-one of Formula-VIII

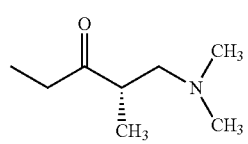

Formula-VIII with 3-bromo anisole of Formula-II

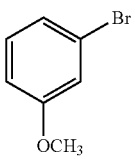

Formula-II using Grignard reaction condition to get the compound (2S,3R)-1-(dimethylamino)-3-(3-methoxyphenyl)-2-methyl pentan-3-ol of Formula-V.

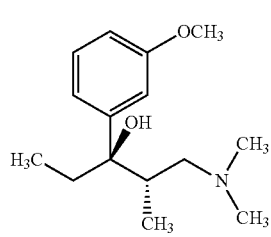

Formula-V

The compound (2S,3R)-1-(dimethylamino)-3-(3-methoxyphenyl)-2-methyl pentan-3-ol of Formula-V is further on activation of the OH group is converted to better leaving group to yield the compound of Formula IXA or IXB;

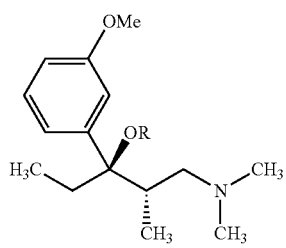

IXA; R=—SO$_2$CH$_3$;
IXB; R=—SO$_2$.C$_6$H$_4$.CH$_3$

The compound of Formula IXA or IXB on reductive deoxygenation in presence of catalyst yields the compound of Formula VII;

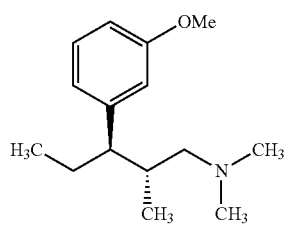

Formula-VII

The compound of Formula VII on demethylation yields the compound 3-[(2R,3R)-1-(dimethylamino)-2-methylpentan-3-yl]phenol of Formula-I.

In an aspect, the process of the present invention provides a novel intermediate compound (2S,3R)-1-(dimethylamino)-3-(3-methoxyphenyl)-2-methylpentan-3-yl methane sulfonate of Formula IXA;

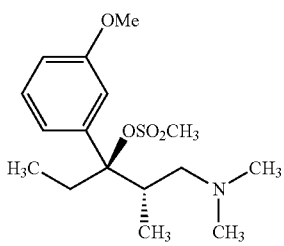

Formula-IXA

In another aspect, the process of the present invention discloses a novel intermediate compound (2S,3R)-1-(dimethylamino)-3-(3-methoxyphenyl)-2-methyl-pentan-3-yl 4-methylbenzenesulfonate of Formula IXB;

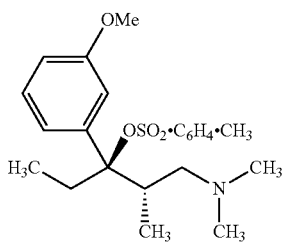

Formula-IXB

The details of one or more embodiments of the present invention are set forth in the description below. Other features, objects and advantages of the invention will be apparent from the appended examples and claims.

DESCRIPTION OF THE INVENTION

The present invention provides a process for the preparation of 3-[(2R,3R)-1-(dimethylamino)-2-methylpentan-3-yl] phenol of Formula-I and its pharmaceutically acceptable salt.

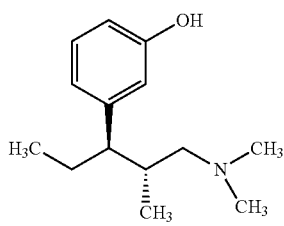

Formula-I

In an embodiment of the present invention the compound (2S,3R)-1-(dimethylamino)-3-(3-methoxyphenyl)-2-methyl pentan-3-ol of Formula-V is prepared by carrying out Grignard reaction of (S)-1-(dimethylamino)-2-methylpentan-3-one of Formula-VIII with 3-bromo anisole of Formula-II in presence of solvent at temperature of 20° C.-80° C. The preferred temperature for the reaction is 20° C. to 60° C., wherein the most preferred temperature for the reaction is 20-35° C. The solvent used for Grignard reaction is selected from toluene, tetrahydrofuran, methyl tetrahydrofuran, diethyl ether and n-hexane, wherein the preferred solvent is tetrahydrofuran. The preferred temperature for Grignard reaction is 50-70° C., wherein the most preferred temperature for the reaction is 65±5° C.

Accordingly the compound 3-bromo anisole of Formula-II is reacted with magnesium turnings in solvent tetrahydrofuran under nitrogen atmosphere in presence of iodine crystal at a temperature of 65±5° C. The reaction was maintained at 65±5° C. to form the Grignard reagent. After complete formation of the Grignard reagent the reaction mass is cooled to 25° C. and to this charged the compound (S)-1-(dimethylamino)-2-methylpentan-3-one of Formula-VIII maintaining the temperature at 25±5° C. Maintained the reaction at the temperature for 10-12 hours and quenched the reaction mass in ice cold water. Adjusted the pH to 3-4 with dilute acetic acid. Further the pH of the quenched reaction mass was adjusted to 9-10 with ammonia solution. The reaction mass was extracted with di isopropyl ether and separated the organic layer. The organic layer was concentrated under reduced pressure to isolate the compound (2S,3R)-1-(dimethylamino)-3-(3-methoxyphenyl)-2-methyl pentan-3-ol of Formula-V.

The Grignard reaction of the compound (S)-1-(dimethylamino)-2-methylpentan-3-one of Formula-VIII is highly stereospecific and the optical purity of the product obtained after the reaction remains intact. The optical purity of the compound (2S,3R)-1-(dimethylamino)-3-(3-methoxyphenyl)-2-methyl pentan-3-ol of Formula-V is dependent on the optical purity of the starting compound of Formula-VIII.

The compound (S)-1-(dimethylamino)-2-methylpentan-3-one of Formula-VIII can be prepared by employing stereoselective Mannich reaction, wherein 3-pentanone is reacted with formaldehyde and dimethyl amine hydrochloride in presence of L-proline and solvent n-butanol. The reaction sequence can be as shown in scheme-3 below.

Scheme-3

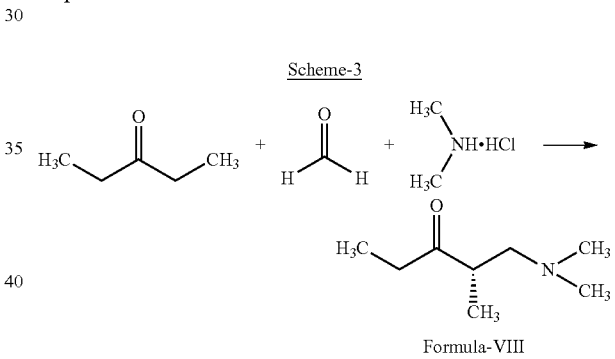

Formula-VIII

In another embodiment of the present invention, the hydroxyl group of the compound (2S,3R)-1-(dimethylamino)-3-(3-methoxyphenyl)-2-methyl pentan-3-ol of Formula-V is activated by converting it into better leaving group. The compound of Formula-V is reacted with methanesulfonic acid or para toluenesulfonic acid in presence of solvent and acid to isolate (2S,3R)-1-(dimethylamino)-3-(3-methoxyphenyl)-2-methyl pentan-3-yl methane sulfonate of Formula IXA or (2S,3R)-1-(dimethylamino)-3-(3-methoxyphenyl)-2-methyl-pentan-3-yl 4-methylbenzenesulfonate of Formula IXB of the compound respectively. The solvent used for the reaction is selected from toluene, tetrahydrofuran, methyl tetrahydrofuran, diethyl ether, cyclohexane and n-hexane or mixture thereof wherein the preferred solvent is tetrahydrofuran and cyclohexane or mixture thereof. The acid used for the reaction is selected from mineral acid selected from hydrochloric acid, sulfuric acid, nitric acid and hydrobromic acid, wherein preferred acid used is sulfuric acid.

Accordingly the compound (2S,3R)-1-(dimethylamino)-3-(3-methoxyphenyl)-2-methyl pentan-3-ol of Formula-V was charged in the solvent tetrahydrofuran and under stirring charged concentrated sulfuric acid at temperature of 20-30° C. The reaction mixture is stirred and charged methanesulfonic acid or para toluenesulfonic acid and solvent cyclohexane. Stirred and raised the temperature to reflux. Maintained the reaction mass at reflux temperature for 3-5 hours with simultaneous removal of water. Cooled the reaction mass to 20° C. and quenched with water. The pH of the quenched reaction solution was adjusted to 8-9 using dilute sodium hydroxide solution. The reaction solution was extracted with cyclohexane. Separated the organic layer and concentrated under reduced pressure to get the compound (2S,3R)-1-(dimethylamino)-3-(3-methoxyphenyl)-2-methyl pentan-3-yl methane sulfonate of Formula IXA or (2S,3R)-1-(dimethylamino)-3-(3-methoxyphenyl)-2-methyl-pentan-3-yl 4-methylbenzenesulfonate of Formula IXB.

In another embodiment of the present invention, the compound of Formula IXA or IXB is subjected to reductive deoxygenation in presence of catalyst and solvent to get the compound (2R,3R)-3-(3-methoxyphenyl)-N,N,2-trimethyl-pentan-1-amine of Formula-VII. The catalyst used for the reductive deoxygenation reaction is metal catalyst selected from palladium on carbon (Pd/C), palladium hydroxide on carbon (Pd(OH)$_2$/C) and palladium dichloride (PdCl$_2$). The preferred catalyst used for reductive deoxygenation is palladium on carbon. The solvents used for the reductive deoxygenation reaction are selected from $C_1$-$C_4$ linear or branched alcohol, tetrahydrofuran, diethyl ether, diisopropyl ether, toluene and cyclohexane or mixture thereof. The preferred solvent used for reductive deoxygenation is tetrahydrofuran and cyclohexane or mixture thereof, wherein the most preferred solvent used is tetrahydrofuran.

The reaction sequence of the present invention is as given below in scheme-4

N,2-trimethylpentan-1-amine of Formula-VII. The catalyst used for the reductive deoxygenation reaction is metal catalyst selected from palladium on carbon (Pd/C), palladium hydroxide on carbon (Pd(OH)$_2$/C) and palladium dichloride (PdCl$_2$). The preferred catalyst used for reductive deoxygenation is palladium on carbon. The solvents used for the reductive deoxygenation reaction are selected from tetrahydrofuran, diethyl ether, diisopropyl ether, toluene and cyclohexane. The preferred solvent used for reductive deoxygenation is tetrahydrofuran and cyclohexane or mixture thereof.

Accordingly the compound (2S,3R)-1-(dimethylamino)-3-(3-methoxyphenyl)-2-methyl pentan-3-ol of Formula-V was charged in the solvent tetrahydrofuran and under stirring charged concentrated sulfuric acid at temperature of 20-30° C. The reaction mixture is stirred and charged methanesulfonic acid or para toluenesulfonic acid and solvent cyclohexane. Stirred and raised the temperature to reflux. Maintained the reaction mass at reflux temperature for 3-5 hours with simultaneous removal of water. Cooled the reaction mass to 20° C. and separated the organic layer. Charged the organic layer in an autoclave and diluted the layer with tetrahydrofuran. Charged the catalyst Pd/C. Purged the autoclave with nitrogen gas and followed with hydrogen gas pressure of 5-7 kg. Maintained the reaction mass at 25-30° C. for 2-4 hours. After completion of the reaction the reaction mass was filtered and the filtrate was concentrated under reduced pressure to get the residual mass. Diluted the residual mass with water and extracted with toluene. Separated the aqueous layer and adjusted the pH to 9-10 with aqueous solution of sodium hydroxide. Extracted the aqueous layer with diiso-

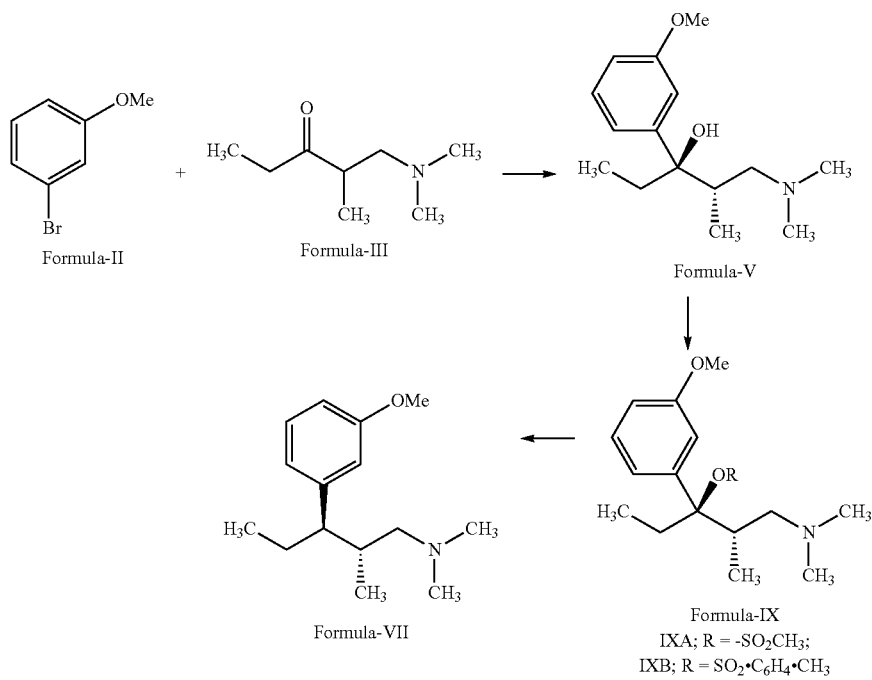

Scheme-4

In another embodiment of the present invention the hydroxyl group of the compound (2S,3R)-1-(dimethylamino)-3-(3-methoxyphenyl)-2-methyl pentan-3-ol of Formula-V is activated by converting it into better leaving group, which on insitu reductive deoxygenation in presence of catalyst yields the compound (2R,3R)-3-(3-methoxyphenyl)-N, propyl ether, separated the organic layer and concentrated under reduced pressure below 40° C. to get the compound (2R,3R)-3-(3-methoxyphenyl)-N,N,2-trimethylpentan-1-amine of Formula-VII.

The reaction sequence of the invention is as given below in scheme-5.

Scheme-5

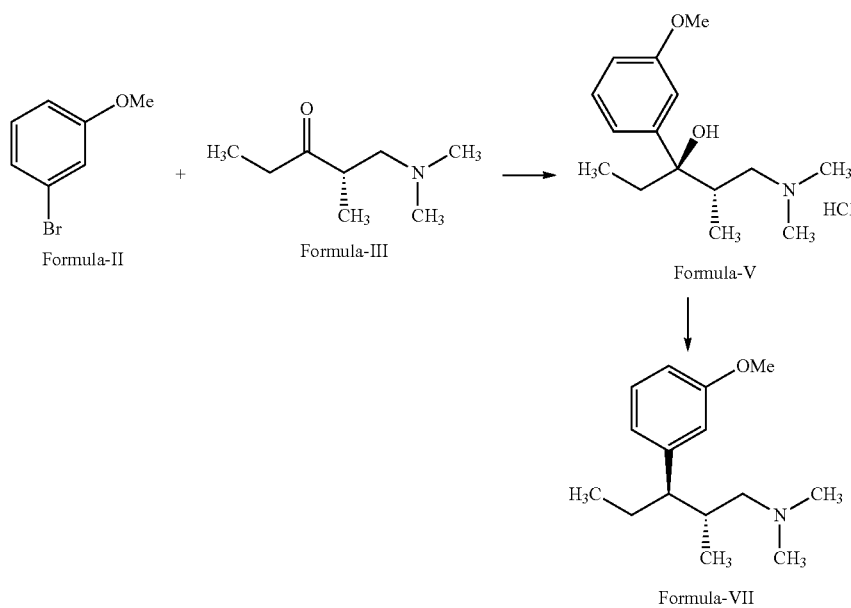

Yet another embodiment of the present invention the compound (2R,3R)-3-(3-methoxyphenyl)-N,N,2-trimethylpentan-1-amine of Formula-VII is subjected to demethylation with dimethyl sulfide in presence of solvent methanesulfonic acid to isolate the compound 3-[(2R,3R)-1-(dimethylamino)-2-methylpentan-3-yl]phenol of Formula-I.

Accordingly the compound (2R,3R)-3-(3-methoxyphenyl)-N,N,2-trimethylpentan-1-amine of Formula-VII was taken in pre cooled methanesulfonic acid and stirred at 0-10° C. Charged dimethyl sulfide to the reaction solution and raised the temperature of the reaction to 55-60° C. Maintained the reaction at 55-60° C. for 2-3 hours and cooled the reaction to 20-30° C. Quenched the reaction mass in ice cold water and extracted the reaction solution with toluene. Separated the aqueous layer and adjusted the pH to 9-10 with dilute aqueous sodium hydroxide solution. Extracted the aqueous layer with toluene and separated the toluene layer. Concentrated the solvent under reduced pressure to isolate the compound 3-[(2R,3R)-1-(dimethylamino)-2-methylpentan-3-yl]phenol of Formula-I.

The pharmaceutically acceptable hydrochloride salt of the compound 3-[(2R,3R)-1-(dimethylamino)-2-methylpentan-3-yl]phenol of Formula-I is prepared by dissolving the compound in solvent isopropanol or acetone and hydrochloric acid gas or adding dissolved hydrochloric acid in respective solvent by a process disclosed in prior arts.

The present invention is further illustrated in detail with reference to the following example. It is desired that the example be considered in all respect as illustrative and are not intended to limit the scope of the claimed invention.

EXAMPLES

Example-1

Preparation of (2S,3R)-1-(dimethylamino)-3-(3-methoxyphenyl)-2-methyl pentan-3-ol In a dry flask charged magnesium turning (41.0 gm 1.70 M) in tetrahydrofuran (200 ml). Under nitrogen atmosphere charged 3-Bromo anisole (20.0 gm; 0.106 M), iodine crystal (0.2 gm). Stirred and heated the reaction mass to 68-75° C. After initiation of the reaction the remaining quantity of 3-Bromo anisole (307 gm, 1.641 M) was added maintaining the reaction at reflux. Stirred and maintained the reaction mass at refluxed for 1 hrs, cooled to 25-30° C. Slowly added (2S)-1-(dimethylamino)-2-methylpentan-3-one (100.0 gm, 0.699 M) maintaining the temperature of the reaction at 25-30° C. The reaction mass was maintained for 12 hour at 25-30° C. and then quenched the reaction mass in ice cold D. M. water (1.0 Liter). Stirred and adjusted the pH of the reaction mass to 3-4 with acetic acid. Further adjusted the pH to 9-10 using ammonia solution. Stirred the reaction mass 30 minutes and extracted the reaction solution with diisopropyl ether. Combined diisopropyl ether was dried over anhydrous sodium sulphate and concentrated under reduced pressure below 40° C. to get the compound (2S,3R)-1-(dimethylamino)-3-(3-methoxyphenyl)-2-methylpentan-3-ol.

Yield=140.0 gm
% Yield=79.77%.

Example-2

Preparation of (2S,3R)-1-(dimethylamino)-3-(3-methoxyphenyl)-2-methylpentan-3-yl 4-methylsulfonate Charged (2S,3R)-1-(dimethylamino)-3-(3-methoxyphenyl)-2-methyl pentan-3-ol (100.0 gm, 0.398 M) and tetrahydrofuran (200 ml) in a dry R.B. Flask. Stirred at 25-30° C. and charged slowly conc. Sulfuric acid (42.94 gm, 0.438 M). Under stirring charged methanesulfonic acid (42.07 gms, 0.438 M) and cyclohexane (300 ml). Raised the temperature of the reaction mass to 78° C. and maintained at 76-80° C. for 3.0 hours with simultaneous removal of water. Quenched the reaction mass with water (500 ml) and adjusted the pH of the aqueous layer to 8-9 with aqueous sodium hydroxide solution. Extracted the aqueous layer with cyclohexane and separated the organic layer. Distilled out solvent under reduced pressure to get the compound ((2S,3R)-1-(dimethylamino)-3-(3-methoxyphenyl)-2-methyl-pentan-3-yl-4-methylsulfonate.

Yield=117.96 gm
% Yield=90.0%.

Example-3

Preparation of (2R,3R)-3-(3-methoxyphenyl)-N,N2-trimethyl pentan-1-amine

Charged ((2S,3R)-1-(dimethylamino)-3-(3-methoxyphenyl)-2-methyl-pentan-3-yl 4-methylsulfonate (100.0 gm, 0.303 M) and tetrahydrofuran (200 ml) in an autoclave. Charged 10% Pd/C (5.06 gm) and flushed the autoclave with nitrogen under stirring. Pressurized the reaction mass with 5.0 kg hydrogen gas. The reaction mass maintained for 2-4 hours at 25-30° C. Filtered the catalyst Pd/C from the reaction mass and filtrate was concentrated under reduced pressure to get residual oil. To the residue charged DM water (200 ml) and washed the solution with toluene. Separated the aqueous layer and cooled to 0-5° C. Adjusted the pH to 9-10 with aqueous sodium hydroxide solution. The above reaction mass was extracted with 3×200 ml diisopropyl ether and separated the organic layer. Combined organic layer was concentrated under reduced pressure to get the compound (2R,3R)-3-(3-methoxyphenyl)-N,N2-trimethyl pentan-1-amine.

Yield=65.0 gm
% Yield=91.0%.

Example-4

Preparation of (2R,3R)-3-(3-methoxyphenyl)-N,N2-trimethylpentan-1-amine

Charged (2S,3R)-1-(dimethylamino)-3-(3-methoxyphenyl)-2-methyl pentan-3-ol (100.0 gm, 0.398 M) and tetrahydrofuran (200 ml) in a dry R.B. Flask. Stirred at 25-30° C. and charged slowly conc. Sulfuric acid (42.94 gm, 0.438 M). Under stirring charged methanesulfonic acid (42.07 gm, 0.438 M) and cyclohexane (300 ml). Raised the temperature of the reaction mass to 78° C. and maintained at 76-80° C. for 3.0 hours with simultaneous removal of water. Cooled the reaction mass to 25-30° C. and separated the organic layer. Charged the organic layer in an autoclave and diluted the layer with fresh tetrahydrofuran (200 ml). Charged 10% Pd/C (5.0 gm) and flushed the autoclave with nitrogen under stirring. Pressurized the reaction mass with 5.0 kg hydrogen gas. The reaction mass maintained for 2-4 hours at 25-30° C. Filtered the catalyst Pd/C from the reaction mass and filtrate was concentrated under reduced pressure below 40° C. to get residual oil. To the residue charged DM water (200 ml) and washed the solution with toluene. Separated the aqueous layer and cooled to 0-5° C. Adjusted the pH to 9-10 with aqueous sodium hydroxide solution. The above reaction mass was extracted with 3×200 ml diisopropyl ether and separated the organic layer. Combined organic layer was concentrated under reduced pressure to get the compound (2R,3R)-3-(3-methoxyphenyl)-N,N2-trimethyl pentan-1-amine.

Yield=80.0 gm
% Yield=93.62%.

Example-5

Preparation of (2R,3R)-3-(3-Hydroxyphenyl)-N,N2-trimethyl pentan-1-amine [Tapentadol]

Charged methane sulfonic acid (300 ml) and cooled to 5-10° C. Maintaining the temperature at 5-10° C. slowly charged the compound (2R,3R)-3-(3-methoxyphenyl)-N,N 2-trimethyl pentan-1-amine (60 gm, 0.255M) and stirred at 5-10° C. for 10 minutes. Charged dimethyl sulfide (30.0 ml) and raised the temperature of the reaction mass to 55-60° C. Maintained the reaction for 2 hours at 55-60° C. Stopped heating and cooled the reaction to 25-30° C. and quenched the reaction mass in ice cold water (900 ml). Extracted the reaction solution with toluene and separated the aqueous layer. Collected aqueous layer and cooled to 5° C. Adjusted pH of the aqueous layer to 9-10 with aqueous sodium hydroxide solution. Extracted the solution with toluene (2×100 ml). Combined the toluene layer and concentrated under reduced pressure to get the compound (2R,3R)-3-(3-Hydroxyphenyl)-N,N2-trimethyl pentan-1-amine [Tapentadol free base].

Yield=50.0 gm
% Yield=88.62%.

Example-6

Preparation of (2R,3R)-3-(3-Hydroxyphenyl)-N,N2-trimethyl pentan-1-amine hydrochloride [Tapentadol Hydrochloride]

Charged (2R,3R)-3-(3-Hydroxyphenyl)-N,N2-trimethylpentan-1-amine (50 gm, 0.226M) in 100 ml acetone. Hydrochloric acid gas was purged maintaining the temperature at 20-30° C. till pH of the reaction mass becomes 6-6.5. The reaction mass was maintained under stirring for 2 hrs at 20-25° C. and filtered. The product was washed with chilled acetone and dried at 50-55° C. to yield (2R,3R)-3-(3-Hydroxyphenyl)-N,N2-trimethyl pentan-1-amine hydrochloride. (Tapentadol Hydrochloride).

Yield=25.0 gm
% Yield=42.91%.

We claim:
1. A process for the preparation of 3-[(R2R,3R)-1-(dimethylamino)-2-methylpentan-3-yl]phenol of Formula-I or its pharmaceutically acceptable salt,

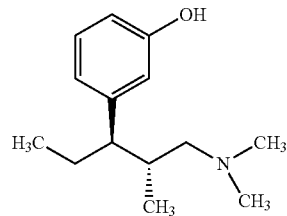

Formula-I said process comprising:
a) reacting (S)-1-(dimethylamino)-2-methylpentan-3-one of Formula-VIII with 3-bromo anisole of Formula-II under Grignard reaction conditions to obtain the compound (2S,3R)-1-(dimethylamino)-3-(3-methoxyphenyl)-2-methyl pentan-3-ol of Formula-V; and

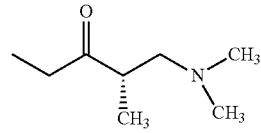

Formula-VIII

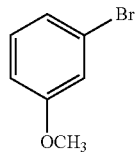
Formula-II

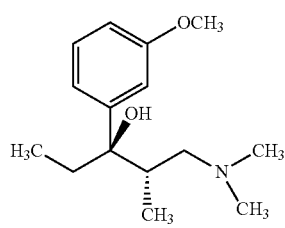
Formula-V b) activating the —OH group of (2S,3R)-1-(dimethylamino)-3-(3-methoxyphenyl)-2-methyl pentan-3-ol with methanesulfonic acid or para-toluenesulfonic acid in the presence of a solvent and a mineral acid to obtain

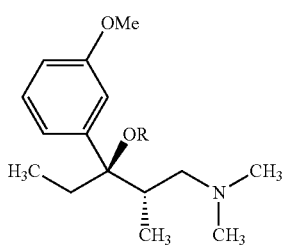
Formula IX an activated compound of Formula IX where R=–SO$_2$CH$_3$ or R=—SO$_2$C$_5$H$_4$CH$_3$; and c) demethylating the activated compound to obtain 3-[(2R,3R)-1-(dimethylamino)-2-methylpentan-3-yl]phenol of Formula-I.

2. The process for the preparation of 3-[(2R,3R)-1-(dimethylamino)-2-methylpentan-3-yl]phenol of Formula-I according to claim 1, wherein said demethylating comprises
   i. reductive deoxygenation of the activated compound in the presence of catalyst to get the compound (2R,3R)-3-(3-methoxyphenyl)-N,N,2-trimethylpentan-1-amine of Formula VII and

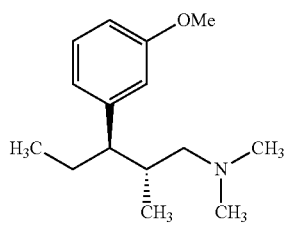
Formula VII ii. demethylating the compound of Formula VII to obtain the compound 3-[(2R,3R)-1-(dimethylamino)-2 methylpentan-3-yl]phenol of Formula-I.

3. The process according to claim 1, wherein said reacting under Grignard reaction conditions is performed in a solvent selected from the group consisting of toluene, tetrahydrofuran, methyl tetrahydrofuran, diethyl ether and n-hexane.

4. The process according to claim 1, wherein Grignard reaction is carried out at temperature of 20-80° C.

5. The process according to claim 1, wherein activation of —OH group of formula V is carried out with methanesulfonic acid in presence of solvent and mineral acid to isolate the compound (2S,3R)-1-(dimethylamino)-3-(3-methoxyphenyl)-2-methyl-pentan-3-yl methane sulfonate.

6. The process according to claim 1, wherein activation of —OH group of formula V is carried out with para toluenesulfonic acid in presence of solvent and mineral acid to isolate the compound (2S,3R)-1-(dimethylamino)-3-(3-methoxyphenyl)-2-methyl-pentan-3-yl 4-methylbenzenesulfonate.

7. The process according to claim 1, wherein the activation of —OH group is carried out in a solvent selected from the group consisting of toluene, tetrahydrofuran, methyl tetrahydrofuran, diethyl ether, cyclohexane, n-hexane and mixtures thereof.

8. The process according to claim 1, wherein the mineral acid is selected from the group consisting of hydrochloric acid, sulfuric acid and hydrobromic acid.

9. The process according to claim 2, wherein the catalyst used for the reductive deoxygenation reaction is metal catalyst selected from the group consisting of palladium on carbon (Pd/C), palladium hydroxide on carbon (Pd(OH)$_2$/C) and palladium dichloride (PdCl$_2$).

10. The process according to claim 2, wherein the reductive deoxygenation reaction is carried out in a solvent selected from the group consisting of C$_1$-C$_4$ linear or branched alcohol, tetrahydrofuran, diethyl ether, diisopropyl ether, toluene, cyclohexane and mixtures thereof.

11. The process according to claim 2, wherein the demethylation of compound of formula VII is carried out with dimethyl sulfide in presence of methanesulfonic acid as solvent to isolate the compound 3-[(2R,3R)-1-(dimethylamino)-2-methylpentan-3-yl]phenol of Formula-I.

12. A process for the preparation of 3-[(2R,3R)-1-(dimethylamino)-2-methylpentan-3-yl]phenol of Formula-I or its pharmaceutically acceptable salt, comprising;

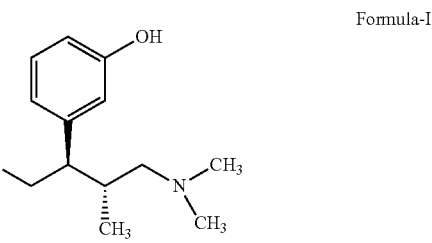
Formula-I a) reacting (S)-1-(dimethylamino)-2-methylpentan-3-one of Formula-VIII with 3-bromo anisole of Formula-II under Grignard reaction condition to obtain compound (2S,3R)-1-(dimethylamino)-3-(3-methoxyphenyl)-2-methyl pentan-3-ol of Formula-V;

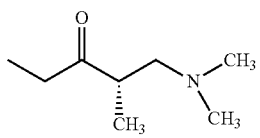

Formula-VIII

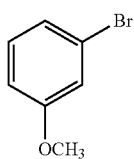

Formula-II

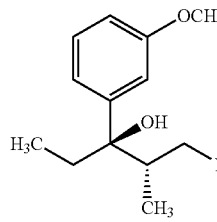

Formula-V b) activating the —OH group of (2S,3R)-1-(dimethylamino)-3-(3-methoxyphenyl)-2-methyl pentan-3-ol with methanesulfonic acid or para toluenesulfonic acid in the presence of a solvent and a mineral acid to obtain

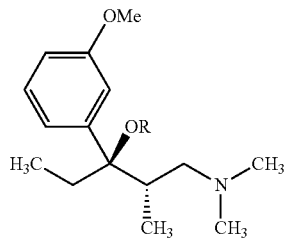

Formula IX an activated compound of Formula IX wherein R=—SO$_2$CH$_3$ or R=—SO$_2$C$_5$H$_4$CH$_3$; and c) carrying out insitu reductive deoxygenation of the activated compound to obtain the compound (2R,3R)-3-(3-methoxyphenyl)-N,N,2-trimethylpentan-1-amine of Formula VII;

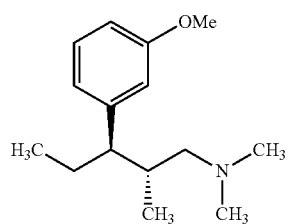

Formula VII d) demethylating the compound of Formula VII to obtain the compound of Formula-I; and e) optionally converting the compound of Formula-I into an acid addition salt.

13. The process according to claim 12, wherein the catalyst used for the insitu reductive deoxygenation reaction is metal catalyst selected from palladium on carbon (Pd/C), palladium hydroxide on carbon (Pd (OH)$_2$/C) and palladium dichloride (PdCl$_2$).

14. The process according to claim 12, wherein the insitu reductive deoxygenation reaction is carried out in a solvent selected from the group consisting of tetrahydrofuran, diethyl ether, diisopropyl ether, toluene, cyclohexane and mixtures thereof.

15. The process according to claim 12, wherein the acid addition salt of the compound 3-[(2R,3R)-1-(dimethylamino)-2-methylpentan-3-yl]phenol of Formula-I is hydrochloride salt.

* * * * *

UNITED STATES PATENT AND TRADEMARK OFFICE
CERTIFICATE OF CORRECTION

PATENT NO. : 8,853,456 B2
APPLICATION NO. : 13/816292
DATED : October 7, 2014
INVENTOR(S) : Mangresh Narayan Rajadhyaksha et al.

It is certified that error appears in the above-identified patent and that said Letters Patent is hereby corrected as shown below:

IN THE CLAIMS

In column 14, line 37-39, replace "A process for the preparation of 3-[(R2R,3R)-1-(dim-ethylamino)-2-methylpentan-3-yl]phenol of Formula-I or its pharmacuetically acceptable salt," with --- A process for the preparation of 3-[(2R,3R)-1-(dim-ethylamino)-2-methylpentan-3yl[phenol of Formula-I or its pharmaceutically acceptable salt, ---

In column 15, line 41, replace "R=–SO$_2$C$_5$H$_4$CH$_3$" with --- "R= –SO$_2$C$_5$H$_4$CH$_3$ ---

In column 18, line 2, replace "R=–SO$_2$CH$_3$ or R=–SO$_2$C$_5$H$_4$CH$_3$" with --- R= –SO$_2$CH$_3$ or R= –SO$_2$C$_5$H$_4$CH$_3$ ---

Signed and Sealed this
Sixth Day of January, 2015

Michelle K. Lee
*Deputy Director of the United States Patent and Trademark Office*